United States Patent [19]

Spangler et al.

[11] Patent Number: 5,338,931
[45] Date of Patent: Aug. 16, 1994

[54] PHOTOIONIZATION ION MOBILITY SPECTROMETER

[75] Inventors: Glenn E. Spangler, Lutherville; Joseph E. Roehl, Baltimore, both of Md.; Gautam B. Patel, New Freedom, Pa.; Alvin Dorman, Baltimore, Md.

[73] Assignee: Environmental Technologies Group, Inc., Baltimore, Md.

[21] Appl. No.: 872,311

[22] Filed: Apr. 23, 1992

[51] Int. Cl.[5] .................. B01D 59/44; H01J 49/00
[52] U.S. Cl. ........................ 250/287; 250/423 P
[58] Field of Search ............... 250/281, 282, 286, 287, 250/288, 423 P

[56] References Cited

U.S. PATENT DOCUMENTS

| | | | |
|---|---|---|---|
| 2,950,387 | 8/1960 | Brubaker | 250/423 P |
| 3,626,181 | 12/1971 | Wernlund | 250/287 |
| 4,378,499 | 3/1983 | Spangler et al. | 250/287 |
| 4,413,185 | 11/1983 | Leveson et al. | 250/423 P |
| 4,551,624 | 11/1985 | Spangler et al. | 250/287 |
| 4,797,554 | 1/1989 | Blanchard et al. | 250/287 |
| 5,032,721 | 7/1991 | Bacon et al. | 250/287 |
| 5,095,206 | 3/1992 | Bacon et al. | 250/287 |

*Primary Examiner*—Bruce C. Anderson
*Attorney, Agent, or Firm*—Bernard A. Reiter & Associates

[57] ABSTRACT

An improved photoionization ion mobility spectrometer is disclosed which utilizes a flashlamp as the source for ionization. A gas sample is introduced via a carrier gas into a ionization chamber which is part of the spectrometer cell. Ionizable molecules contained in the injected gas sample are ionized by the ultraviolet light emitted from the flashlamp. The ionized molecules are attracted by an electrostatic drift field into a drift chamber and travel therethrough against the flow of a drift gas counter-current thereto until they are captured by a collector located in the drift chamber opposite to the ionization chamber. A dopant with an effective ionization potential lower than the photon energy of the emitted light can be introduced into the ionization chamber to further improve the sensitivity and specificity.

24 Claims, 6 Drawing Sheets

PHOTOIONIZATION ION MOBILITY SPECTROMETER

GOVERNMENT INTEREST

The U.S. Government has rights in this invention pursuant to Contract DAA15-90-C-0030, awarded by the U.S. Army.

BACKGROUND OF THE INVENTION

This invention relates to a photoionization ion mobility spectrometer for the detection of ionizable chemical species. More particularly, this invention relates to an improved photoionization ion mobility spectrometer system utilizing flashlamp technology as the ionization source.

Ion mobility spectrometry is a technology to detect and identify the presence of an ionizable chemical species, and provide quantitative information. Conventionally, such an ionizable chemical species is ionized using a radioactive source. The ionized samples, which can be positively or negatively charged, are then subject to an electrostatic field which causes the ions to migrate against a counter current flow of a drift gas. Different chemical species migrate with different mobilities and arrive at an ion collector with different elapsed times. Data from such an ion collector can be stored and analyzed to provide information about the ionized chemical species in terms of the elapsed time, and the quantity of the ionizable chemical species contained in the test sample.

Beta particles from a $^{63}$Ni radioactive source generates reactant ions which ionize the chemical species. The use of a radioactive source limits the acceptance of ion mobility spectrometry in the market place due to licensing and waste disposal requirements. Furthermore, an ionizer based on radioactivity provides little specificity for ionization and the ion mobility spectrometer suffers severe interferences, often caused by false positives and false negatives, and matrix effects from components in complex samples. U.S. Pat. Nos. 4,839,143 and 4,928,033 disclosed the use of alkali cation emitters as an ionization source to replace the radioactive source in ion mobility spectrometry. With the alkali cation emitters, ionization can be accomplished in the positive ion mode but not the negative ion mode. Therefore, a large number of electronegative chemical species could not be detected with a ion mobility spectrometer using alkali emitter as the ionization source. Furthermore, significantly high power (greater than one Watt) was required to heat the alkali emitters to the operating temperature (600–800 degrees Celsius).

U.S. Pat. No. 3,933,432 disclosed a low pressure gas filled lamp that excites $H_2$, Kr, or Xe in a capillary arc discharge to generate the required vacuum ultraviolet radiation for photoionization. Replacing the $^{63}$Ni radioactive ionization source with a photoionization source removes the radioactive hazard. In the '432 patent, the vacuum ultraviolet radiation generated is transmitted through a magnesium fluoride or lithium fluoride window. U.S. Pat. No. 3,904,907 disclosed the use of a helium resonance lamp excited with radio frequency energy. The lamp contains a gettering material to continuously purify the helium. A window, such as aluminum, is provided to pass the desired radiation. U.S. Pat. No. 4,413,185 disclosed the use of a radio frequency inductively coupled discharge lamp with a magnesium fluoride, lithium fluoride, barium fluoride, strontium fluoride, calcium fluoride, or sapphire window. In the '185 patent, finely divided barium is included in the discharge tube as a getter. U.S. Pat. No. 3,699,333 disclosed the possibility of coupling a vacuum ultraviolet lamp to an ion mobility spectrometer. Baim, Eatherton, and Hill in "Ion Mobility Detector for Gas Chromatography With a Direct Photoionization Source", Anal. Chem., Vol. 55, PP. 1761–1766 (1983), disclosed coupling continuously operated photoionization lamps to an ion mobility spectrometer. They used a 10.0 eV (123.6 nm) krypton lamp mounted perpendicular (side-mount) to the direction of gas flow through the cell. Leasure, Fletscher, Anderson, and Eiseman in "Photoionization in Air With Ion Mobility Spectrometry Using a Hydrogen Discharge Lamp", Anal. Chem., Vol. 58, PP. 2142–247 (1986), also similarly disclosed using continuously operated photoionization lamps in an ion mobility spectrometer. They used a 10.2 eV hydrogen discharge lamp mounted coaxial (on axis) to the direction of gas flow through the cell. The results of their experiments showed that the sensitivity and limits of detection were about 1% to 10% of that achieved using the radioactivity source.

U.S. Pat. No. 3,626,181 disclosed the use of a pulsed ultraviolet light source to irradiate an electrode to produce ionized samples. The pulsed ion-producing light source was synchronized with a continuous loop magnetic tape recorder, such that the output signal following each pulse of ultraviolet light was recorded in precisely the same position, and consecutive output signals could be superimposed. Stimac, Cohen, and Wernlund in a government report entitled "Tandem Ion Mobility Spectrometer for Chemical Agent Detection, Monitoring, and Alarm", CRDEC-CR-88082, disclosed an ion mobility spectrometer in which a pulse generator is connected through a pulse transformer to a capillary arc photoionization lamp. Their pulse transformer was triggered synchronously with the ion mobility spectrometer shutter-grid drive circuits with adjustable delays between the grid drive and the lamp pulses. Krypton and xenon lamps were used in their study. Both lamps fired regularly when the repetition period was 15 ms or less. However, they became irregular with a 30 ms repetition, and very erratic with a 100 ms repetition. A 3 second to 30 second interval was needed to initially fire the lamps after being turned off several minutes or longer. In summary, great difficulties were encountered during their attempts to use pulsed photoionization technique in conjunction with ion mobility spectrometer. Furthermore, the purpose of pulsing a capillary arc photoionization lamp was to conserve energy, it was not intended to address specificity or sensitivity.

U.S. Pat. No. 4,551,624 disclosed the introduction of a chemical reagent, such as acetone and/or carbon tetrachloride, into the carrier gas (of an ion mobility spectrometer) to improve the specificity. U.S. Pat. No. 5,032,721 disclosed the addition of a controlled concentration of a dopant substance to the air carrier gas stream prior to application of the carrier gas stream to improve the detection of an acid gas analyte using an ion mobility spectrometer. In both patents, beta-particle ionizing radiation was used to generate product ions from the sample gas introduced into the ion mobility spectrometer by the carrier gas.

Ionization of acetone vapors when they are submitted to photoionization was disclosed by Luczynski and Wincel in an article entitled "Reaction of the Solvated Photon System H+·[(CH₃)₂CO]ₙ Formed in Photoionization of Acetone". Int'l J. Mass Spectrometry and Ion Physics, Vol. 23, PP. 37–44 (1977), and Tzeng, Wei and Castleman, Jr., in another article entitled "Multiphoton Ionization of Acetone Clusters: Metastable Unimolecular Decomposition of Acetone Cluster Ions and the Influence of Solration on Intracluster Ion-Molecule Reactions", J. Am. Chem. Soc., Vol. 111, PP. 6035–6040 (1989). In these two papers it was concluded that protonated monomer, $H^+(CH_3)_2CO$, and dimer, $H^+[(CH_3)_2CO]_2$ ions were formed.

SUMMARY OF THE INVENTION

The primary object of this invention is to provide an ion mobility spectrometer that does not require the use of radioactivity as an ionization source, yet preserving and/or enhancing the specificity and sensitivity thereof.

Another object of this invention is to provide an ion mobility spectrometer that is convenient and safe to use, and can be designed into a portable detector unit.

Another object of the invention is to provide an ion mobility spectrometer that utilizes flashlamp technology as a photoionization source to minimize power consumption, yet is capable of providing satisfactory results for the detection of ionizable chemical species.

Yet another object of this invention is to provide an ion mobility spectrometer that can be conveniently used as a portable field unit to detect the presence of a trace amount of a pre-identified chemical species and give early warning signals.

Yet another object of this invention is to provide an ion mobility spectrometer that can be readily adapted for use as a detector with a gas chromatograph.

This invention relates to an improved ion mobility spectrometer in which a flashlamp system is utilized as the ionization source. The flashlamp contains two discharge electrodes and one or more trigger probes. The trigger probes are connected to a pulse transformer and the discharge electrodes are connected to a source of high voltage (i.e., a rechargeable capacitor). In the non-ionized state, the flashlamp has high impedance. With the application of a trigger pulse, a high electrical potential is place on the trigger probes causing gaseous breakdown to occur in the working gas of the lamp. The impedance of the flashlamp drops and a confined discharge is sustained between the discharge electrodes until the energy stored in the capacitor is dissipated and the flashlamp deionizes. Intense vacuum ultraviolet light is emitted by the lamp during each discharge or flash. The intensity of the emission is related to the energy $(E = \frac{1}{2}CV^2)$ stored in the capacitor before it is discharged.

With the flashlamp disclosed in this invention, the emission of light, or the photon energy, is spontaneous after the trigger which can be supplied at any time electronically. With this invention, the photoionization source does not suffer from the erratic firing behavior noted in the prior art attempts using a pulsed capillary arc lamp. Furthermore, the power consumed in the present invention is only a small fraction of what would be required for a continuously operated dc lamp and is proportional to the energy stored in the capacitor.

To further improve the sensitivity of the ion mobility spectrometer, this invention further discloses the use of a dopant to be introduced into the carrier stream. The dopant to be used in this invention has an ionization potential less than the photon energy emitted by the flashlamp corresponding to the wavelength of the emitted light. With a krypton lamp, the photon energy is 10.0–10.2 eV; therefore, the dopant should have an effective ionization potential less than 10.0 eV. If an argon lamp is used (having a photon energy of 11.7 eV), other dopants with higher effective ionization potentials can be used. The use of such a dopant not only improves specificity of the ion mobility spectrometry, it also enhances sensitivity when a photoionization source is used to generate ionized samples. One reason that the dopant increases sensitivity is the result of the larger ionization cross-section provided by the dopant ions compared to photons. Ions have larger cross-sections because the electric field radiated by the ionic charge induces an opposite charge in the sample molecule. This induced charge causes the molecule to be attracted to and cluster with the ion to form a new product ion. Such an induced dipole interaction makes ion-molecule reactions in the gas phase among the fastest chemical reactions. It is not necessary, however, that the dopant have a true ionization potential lower than the photon energy. An excited dopant can be generated which is ionized by subsequent reactions. Therefore, the criterion for selecting a proper dopant is the "effective" ionization potential of a molecule, and is not necessarily limited to the "true" ionization potential.

The addition of dopant can improve the sensitivity of the ion mobility spectrometer in both the positive mode and negative mode.

DETAILED DESCRIPTION OF THE PREFERRED EMBODIMENT

Figure 1:
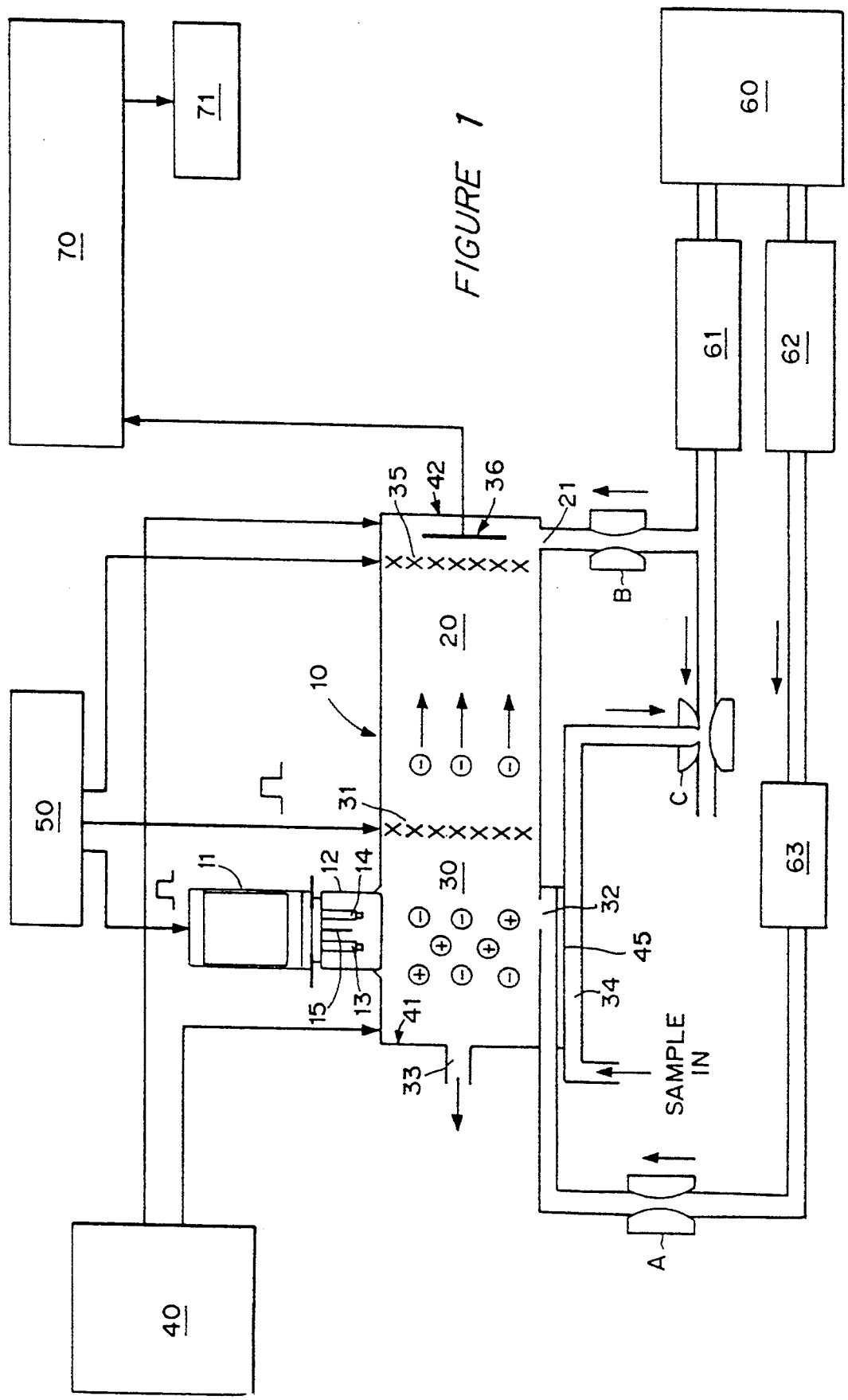
FIG. 1 is a schematic showing the block diagram of a preferred embodiment of the present invention.

Now referring to FIG. 1, which is a schematic of a preferred embodiment of the present invention. The photoionization ion mobility spectrometer of the present invention comprises a main chamber 10, which is separated into a photoionization chamber 30 and a drift chamber 20 by an ion shutter grid 31. A bulb-like flashlamp 12 is mounted sideways in the photoionization chamber and exposed to the interior of the photoionization chamber to emit light thereto. The flashlamp is driven by a pulse transformer 11 which is connected to a controller 50. A drift gas inlet passage 21 allows a drift gas to enter the drift chamber 20 by a pneumatic means. The pneumatic means comprises a regulated pressure air supply 60 which drives the drift gas through the drift chamber 20, the ion shutter grid 31, which is permeable to the drift gas at all times, and the photoionization chamber 30, then exits the photoionization chamber through an exhaust passage 33. A gas sample is introduced into the photoionization chamber through a gas sample inlet passage 34 which is in communication therewith. In the preferred embodiment the gas sample (which is generally mixed with ambient air) is drawn into a membrane inlet by means of a suction pump or a sampling venturi orifice C. The gas sample permeates a thin polymeric or impregnated microporous membrane 45 and mixes with the carrier gas before entering the photoionization chamber through a carrier gas inlet passage 32, which is also in communication with the photoionization chamber. An alternate embodiment is to eliminate the carrier gas and inject effluent from a gas chromatographic column, not shown, directly into the photoionization chamber 30 by inserting the gas chromatographic column through gas inlet passage 32, or exhaust passage 33.

In the preferred embodiment purified air is used as both the drift gas and the carrier gas. Other gases such as nitrogen can also be used. The oxygen molecules in the air often cause a quenching effect upon the photons. The feed air is first passed through separate scrubbers 61, 62 to remove moisture and other undesirable chemical species. Valves A and B are installed in the carrier gas and the drift gas transfer lines, respectively, to control the flow rate therethrough.

During the operation, valves A and B are adjusted to provide desired suitable flow rates for the carrier gas and the drift gas. When a steady state is achieved, the sample gas to be analyzed is drawn or injected into the gas sample inlet passage 34. After permeating membrane 45, the sample gas is carried into the photoionization chamber by the carrier gas. Ionizable chemical species contained in the sample gas are ionized by the bombardment of photons emitted from the flashlamp 12. The ionized gas molecules are then caused to drift by an electrostatic drift field, which is created by applying a high voltage potential between two electrodes 41, 42. The ion shutter grid 31 is an array of parallel wires with every other wire at equal potentials (shutter grid on) or (shutter Grid off). It is controlled electrically to interrupt the electrical field thereby causing the migration of the ionized gas samples to be stopped or continued. The shutter is normally off to prevent ions Generated in the photoionization chamber from entering the drift chamber 20. For the detection of negative ions as shown in FIG. 1, the shutter grid is biased with different potentials for the major part of the measurement to block the entrance of the ionized gas vapors therethrough. At the beginning of the measurement, the controller 50 provides a signal to open shutter grid 31 to admit a cloud of ionized molecules into the drift chamber 30. Under the influence of the electrostatic drift field, the ionized molecules continue their drift towards the ion collector 36. The velocity of the ionized molecules is determined by a balance of forces acting on an ionized molecule by the electrostatic drift field and collisions of the ionized molecule with the drift gas molecules. The time required for the ionized molecule to arrive at the ion collector 36 is dependent on the physical characteristics of the ion (e.g., charge, size and shape). The ion current arriving at the ion collector 36 is also proportional to the concentration of the ions created in photoionization chamber 30. The ion collector 36 is connected to a data acquisition and processing system 70, which may also send a signal to an alarm 71.

The flashlamp 12 shown in FIG. 1 contains two discharge electrodes 13, 14 and one trigger probe 15. The trigger probe is connected to the pulse transformer 11. The discharge electrodes are connected to a capacitor of high energy. In the preferred embodiment the flashlamp 12 is filled with about two atmospheres of noble gas and sealed with a vacuum ultraviolet window. In the preferred embodiment, krypton is used as the noble gas, and a magnesium fluoride window is used as the vacuum ultraviolet window. After a trigger pulse comes from the pulse transformer, the noble gas will be ionized, causing the capacitor to discharge. More than one trigger probe can be placed between the two discharge electrodes 13, 14 to form a guided arc when the capacitor is discharged. When the capacitor is discharged, an arc is formed between the two flashlamp electrodes 13, 14. In the preferred embodiment the arc is unconfined and has a short arc length, and arranged between 1.5 to 8 millimeters. The combination of an unconfined arc and a short arc length results in very low arc impedances. Therefore the pulse durations are very short, typically between 0.7 and 15 microseconds. The flashlamps used in this disclosure were manufactured by EG&G Electro-Optics in Salem, Mass. FIG. 1 shows the flashlamp 12 "side-mounted" with respect to the photoionization chamber 30; it can also be coaxial to the direction of gas flow as disclosed in Leasure, et al., described hereinabove.

As mentioned hereinabove, the ionized gas samples are driven by the electrostatic field against the flow of the drift gas counter-current thereto. The balance between the electrostatic field and the extent of collision determines the mobility of the ionized gas samples toward the detector. The traveling time measured by the detector is a characteristic of the ionized sample. The peak height also gives an indication of the concentration of the ionized gas. A controller 50 is provided to send pulsed signals to the pulse transformer 11 and the ion shutter grid 12. A second ion shutter grid 35 can be optionally placed between the ion detector 36 and the bulk of the drift chamber 20. The second ion shutter grid 35 can also be controlled by a signal received from the controller 50. The flashlamp 12 and the ion shutter grid 31 can be pulsed simultaneously, or the ion shutter grid 31 can have a delayed pulse relative to the flashlamp 12. Furthermore, the shutter grid 31 and the flashlamp 12 can have the same pulse width, or different pulse widths. Similarly, the second optional ion shutter grid 35 can be pulsed simultaneously with the first shutter grid 31 or with a fixed or variable delay relative to the first shutter grid 31. A delay between the first and second shutter grids would allow ions with specific drift times (i.e., mobilities) to be sampled by the ion collector 36. The ion detector 36 is located at the end of the drift chamber 20, opposite the photoionization chamber 30.

To further improve the sensitivity of the photoionization ion mobility spectrometer of this invention, a dopant contained in a dopant chamber 63 can be introduced into the carrier gas stream, preferably before the carrier gas enters the photoionization chamber. The dopant contains chemical species which are ionizable by the photon energy corresponding to the light emitted by the flashlamp. In the preferred embodiment when the flashlamp is filled with krypton and sealed with a magnesium fluoride window, the light of maximum intensity has a photon energy of about 10.0 eV. The dopant is introduced into the carrier gas stream via a blending means incorporating a permeation tube, a diffusion tube, or any other suitable means for controlled release of the dopant.

Figure 2A:
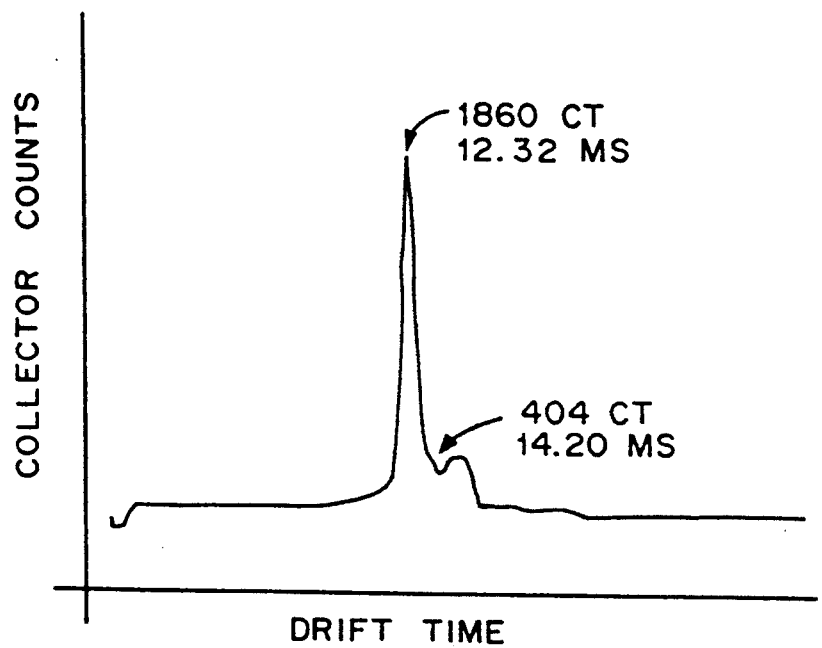
FIGS. 2A and 2B are the plots of detector response versus drift time using a continuous dc lamp and a flashlamp, respectively, measured from saturated acetone vapor.
Figure 2B:
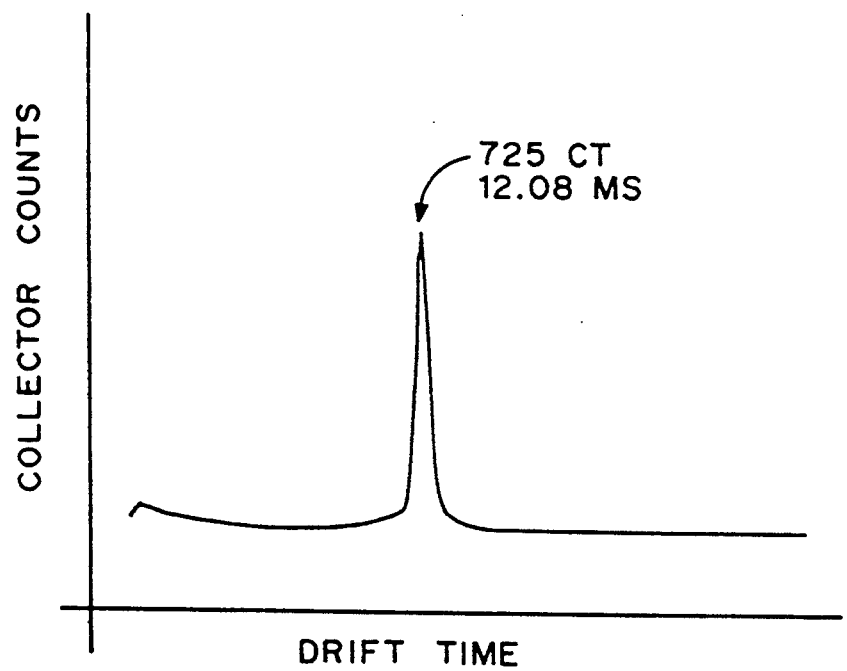

FIGS. 2A and 2B show the measured responses of saturated acetone vapor from an ion mobility spectrometer using a continuous dc lamp, and a flashlamp of this invention, respectively, as the photoionization source. In both measurements, the spectrometer is put in a positive ion mode. For the continuous dc lamp case the flow rate for the carrier gas is 85 cc per minute, and is 300 cc per minute for the drift gas. For the flashlamp case, the flow rate of the carrier gas is 50 cc per minute, and the flow rate for the drift gas is 450 cc per minute. The lamp voltage is 305 volts for the continuous dc lamp and 500 volts for the flashlamp. The power dissipated by the continuous dc lamp and flashlamp was 0.5 and 0.02 watts, respectively. The first peak shows the presence of acetone dimer ion. The continuous dc lamp case shows a greater response from a trimer ion of acetone which is indicated as the latter peak. The higher ultraviolet light intensity available from the flashlamp probably dissociated the acetone trimer ions before they could be sampled into the drift region.

Figure 3A:
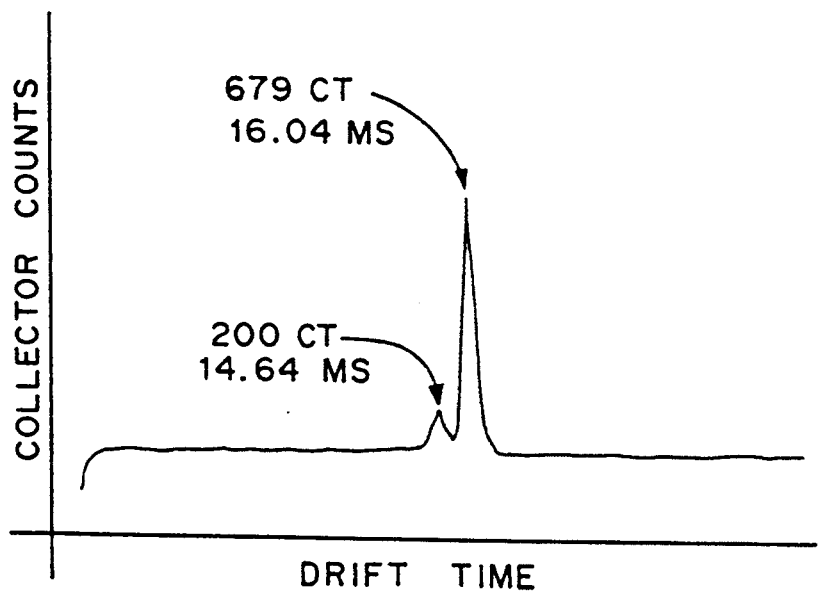
FIGS. 3A and 3B are the plots of detector response versus drift time using a continuous dc lamp and a flashlamp, respectively, measured from saturated DMMP vapor.
Figure 3B:
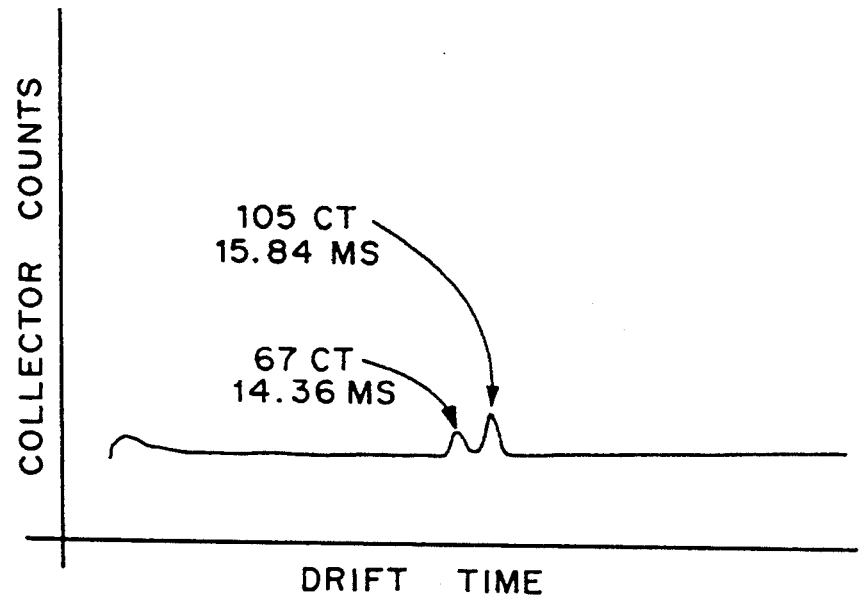

FIGS. 3A and 3B show the measurement results of saturated DMMP (dimethylmethylphosphonate) vapor obtained from a continuous dc lamp and flashlamp respectively, under conditions identical to those described in FIGS. 2A and 2B, respectively. Both results show the monomer ion of DMMP. However, the continuous dc lamp case shows a much stronger response from the dimer ion of DMMP. The reason for the relative absence of the dimer ion is similar to what was described in FIGS. 2A and 2B.

Figure 4A:
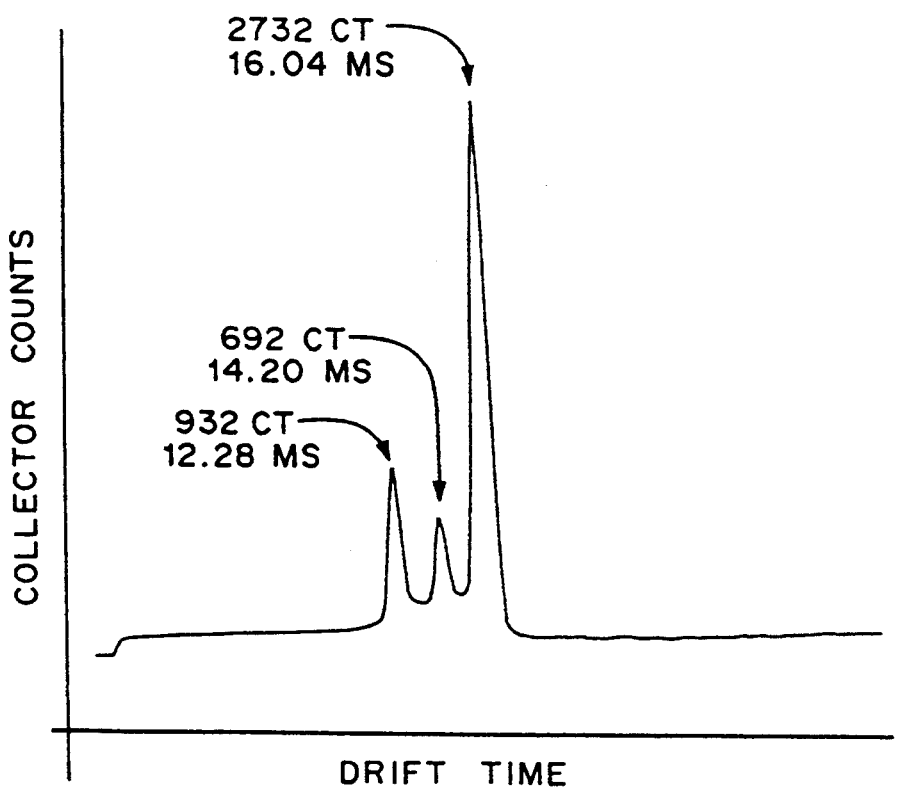
FIGS. 4A and 4B are the plots of detector response versus drift time using a continuous dc lamp and a flashlamp, respectively, measured from a trace concentration of DMMP, using acetone as a dopant.
Figure 4B:
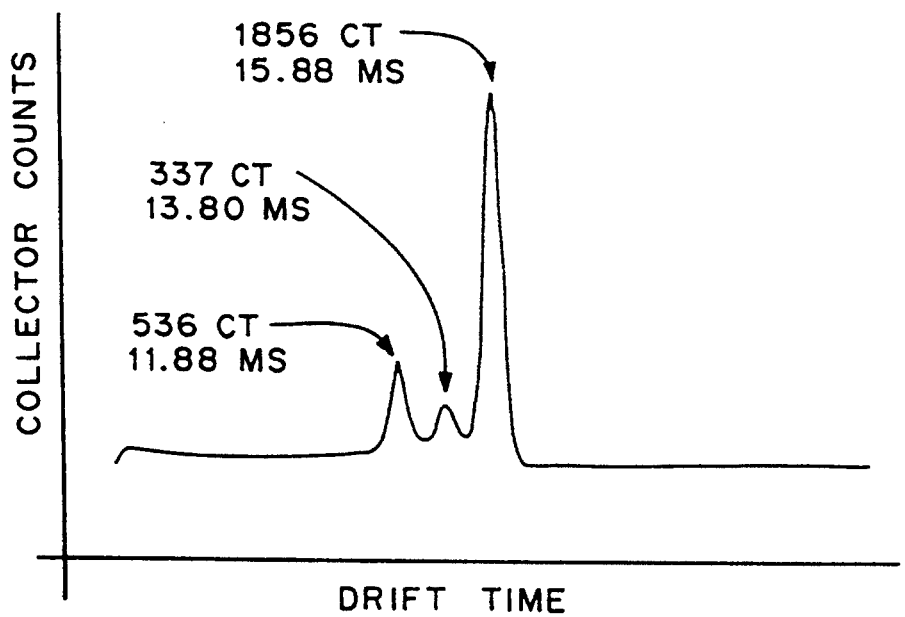

FIGS. 4A and 4B show results from the measurement of a trace concentration of DMMP using a continuous dc lamp and a flashlamp, respectively, as the photoionization source, when 350 parts per million of acetone is added in the carrier gas as a dopant. Without the addition of the acetone dopant, very weak or essentially no response was observed in both cases. The ions with drift times of 12.28 milliseconds (FIG. 4A) and 11.83 milliseconds (FIG. 4B) are protonated dimer ions of acetone which act as reactant ions to ionize the DMMP molecules. The ions with drift times of 14.20 milliseconds (FIG. 4A) and 13.80 milliseconds (FIG. 4B) are mixed clusters of the protonated acetone and DMMP. The ions with drift times 16.04 milliseconds (FIG. 4A) and 15.88 milliseconds (FIG. 4B) are protonated dimer ions of DMMP. With the use of an acetone dopant, the limit of detection for DMMP using photoionization ion mobility spectrometers was approximately 0.047 mg/m$^3$, similar to a $^{63}$Ni radioactive based ion mobility spectrometer. When acetone chemistry is used with a $^{63}$Ni radioactive ion mobility spectrometer, it was found to enhance specificity but not sensitivity. The increase in sensitivity by adding an acetone dopant to either a continuous dc lamp or flashlamp based ion mobility spectrometer is one to two orders of magnitude.

Figure 5A:
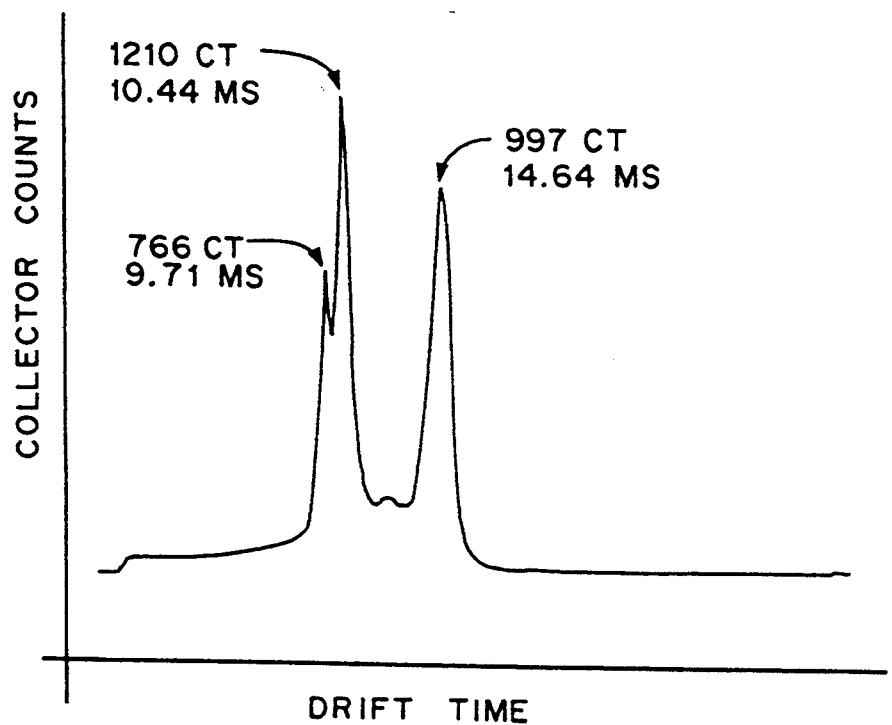
FIGS. 5A and 5B are the plots of detector response versus drift time using a continuous dc lamp and a flashlamp, respectively, measured from a trace concentration of methyl salicylate, using acetone as a dopant.
Figure 5B:
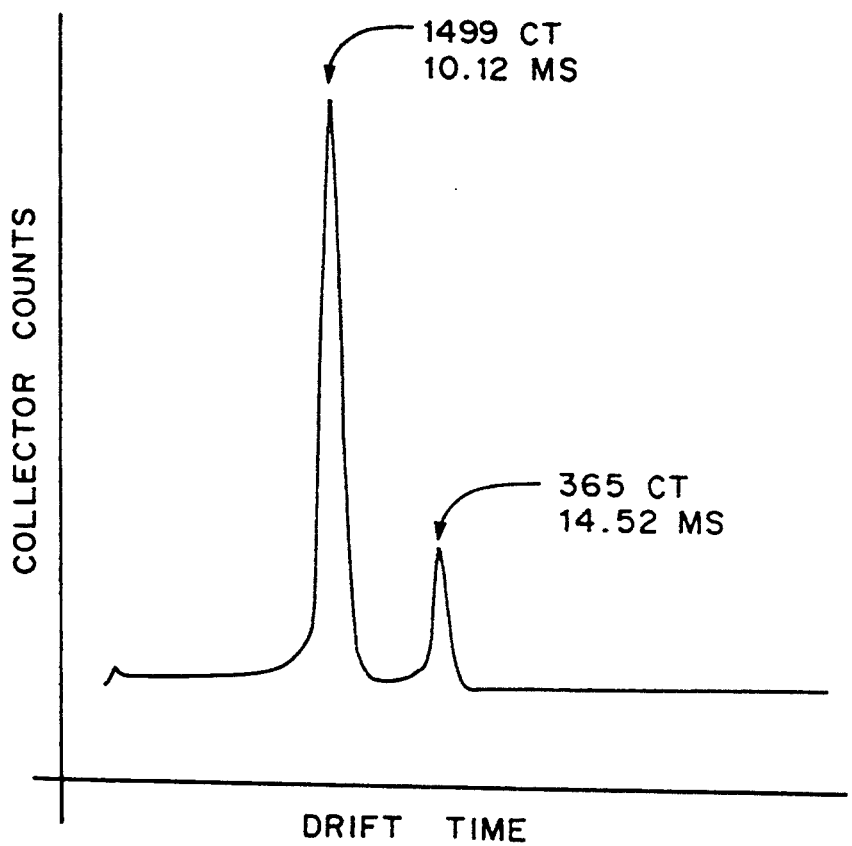

FIGS. 5A and 5B show measurement results from a trace concentration of methyl salicylate (MS) with 500 parts per million of acetone added to the carrier gas as dopant, using a continuous dc lamp and s flashlamp, respectively. The operating parameters are similar to those used in obtain results shown in FIGS. 4A and 4B, respectively, except that the ion mobility spectrometer is now used in the negative ion mode. It is to be noted that the flashlamp case showed a much better response than the dc lamp case. The ions with drift times of 10.44 milliseconds (FIG. 5A) and 10.12 milliseconds (FIG. 5B) are quasimolecular product ions of MS. The limit of detection for MS was 0.006 mg/m$^3$, again comparable to that obtained from a $^{63}$Ni radioactive ion mobility spectrometer.

Figure 6A:
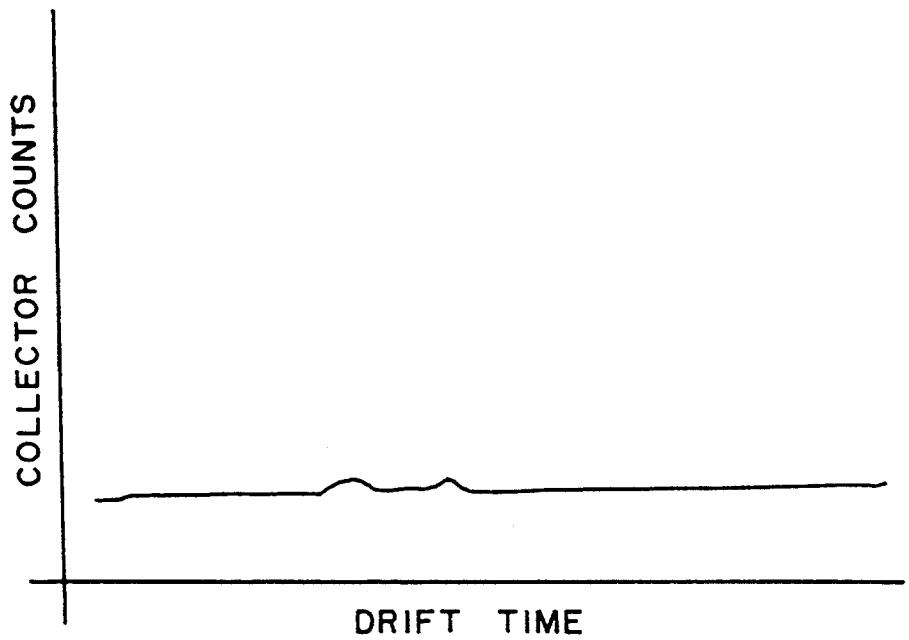
FIGS. 6A and 6B are the plots of detector response versus drift time using a continuous dc lamp and a flashlamp, respectively, measured from a trace concentration of methyl salicylate, without dopant.
Figure 6B:
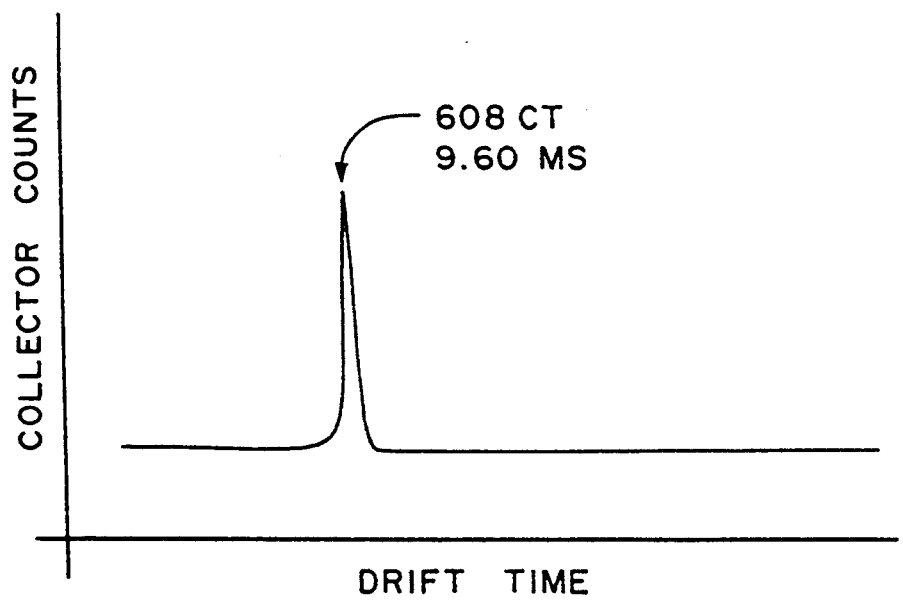

FIGS. 6A and 6B show similar measurements from a trace concentration of methyl salicylate using a continuous dc lamp and a flashlamp, respectively, without the addition of the acetone dopant. No response was observed with the continuous dc lamp; whereas a single peak was observed with the flashlamp case. In FIGS. 5 and 6, because the methyl salicylate ion is negatively charged, the spectrometer is operated in a negative ion mode.

Although the best mode contemplated for carrying out the present invention has been herein shown and described, it will be apparent that modification and variation may be made without departing from what is regarded as the subject matter of the invention. For example, chloride chemistry can be used with flashlamp photoionization in a manner similar to $^{63}$Ni radioactive ion mobility spectrometry. Also, flashlamps filled with working gases other than krypton and sealed with windows, other than magnesium fluoride, can be used to achieve other ionization energies. By choosing an appropriate lamp, selectively of ionization can be improved for specific applications.

What is claimed is:

1. An improved photoionization ion mobility spectrometer system for the detection of ionizable chemical species, comprising:
    (a) a housing having a main chamber therein, said main chamber comprising a photoionization chamber and a drift chamber;
    (b) drift gas inlet passage in communication with said drift chamber for entering a drift gas therethrough;
    (c) an exhaust passage in communication with said photoionization chamber for exiting said drift gas;
    (d) pumping means for forcing said drift gas to travel in said main chamber in a first direction;
    (e) a carrier gas inlet passage in communication with said photoionization chamber for introducing a carrier gas into said photoionization chamber;
    (f) a gas sample inlet means in communication with said photoionizaton chamber for introducing a gas sample to be analyzed into said photoionization chamber;
    (g) a lamp means exposed to said photoionization chamber for ionizing said gas sample therein to form ionized gas sample, said lamp means comprising
        (i) an electrical pulse transformer,
        (ii) a flashlamp filled with about two atmospheres of noble gas and sealed with a window for transmitting light with desired wavelength, and
        (iii) said flashlamp further containing two electrodes and at least one trigger probe, said trigger probe being connected to said pulse transformer and said electrodes being connected to a capacitor of high energy, said capacitor being adapted to discharge when a trigger pulse from said pulse transformer causes an ionization of said noble gas in said flashlamp and a discharge of said capacitor;
    (h) electrode means for driving said ionized gas sample in said main chamber in a second direction countercurrent to said first direction; and (i) detector means placed in said drift chamber for detecting said ionized gas sample.

2. The improved photoionization ion mobility spectrometer of claim 1 wherein said noble gas is krypton.

3. The improved photoionization ion mobility spectrometer of claim 1 wherein said window is a magnesium fluoride window.

4. The improved photoionization ion mobility spectrometer of claim 1 wherein said at least one trigger probe being disposed between said two electrodes to form a guided arc when said capacitor is discharged.

5. The improved photoionization ion mobility spectrometer of claim 1 wherein said flashlamp containing two or more trigger probes disposed between said two electrodes to form a guided arc when said capacitor is discharged.

6. The improved photoionization ion mobility spectrometer of claim 1 wherein said flashlamp is a bulb-type flashlamp having an unconfined arc.

7. The improved photoionization ion mobility spectrometer of claim 1 wherein said flashlamp having a short pulse duration in the microseconds range, typically between 0.7 and 1.5 microseconds, when said capacitor is discharged.

8. The improved photoionization ion mobility spectrometer of claim 1 further comprising an ion shutter grid separating said photoinization and drift chambers, said ion shutter grid being electrically pulsed to allow an intermittent passage of said ionized gas sample therethrough and wherein said flashlamp and said ion shutter grid are pulsed simultaneously.

9. The improved photoionization ion mobility spectrometer of claim 1 further comprising an ion shutter grid separating said photoionization and drift chambers, said ion shutter grid being electrically pulsed to allow an intermittent passage of said ionized gas sample therethrough and wherein said ion shutter grid has a delayed pulse relative to said flashlamp.

10. The improved photoionization ion mobility spectrometer of claim 1 further comprising an ion shutter grid separating said photoionization and drift chambers, said ion shutter grid being electrically pulsed to allow an intermittent passage of said ionized gas sample therethrough and wherein said shutter grid and said flashlamp have the same pulse width.

11. The improved photoionization ion mobility spectrometer of claim 1 further comprising an ion shutter grid separating said photoionization and drift chambers, said ion shutter grid being electrically pulsed to allow an intermittent passage of said ionized gas sample therethrough and wherein said shutter grid and said flashlamp have different pulse width.

12. The improved photoionization ion mobility spectrometer of claim 1 wherein both said drift gas and said carrier gas are purified air.

13. The improved photoionization ion mobility spectrometer of claim 1 wherein said pumping means comprises pneumatic means.

14. The improved photoionization ion mobility spectrometer of claim 1 further comprises separate controlled means for controlling flow rates of said carrier gas and said drift gas into said main chamber.

15. The improved photoionization ion mobility spectrometer of claim 1 further comprising a means for introducing a dopant into said photoionization chamber.

16. The improved photoionization ion mobility spectrometer of claim 15 wherein said means for introducing a dopant into said photoionization chamber comprises a blending means by which said dopant is introduced into said carrier gas using a permeation tube, diffusion tube or other suitable means before said carrier gas enters said carrier gas inlet passage.

17. The improved photoionization ion mobility spectrometer of claim 15 wherein said dopant comprises chemical species having an ionization potential less than the photon energy corresponding to the wavelength of the light of maximum intensity emitted by said flashlamp means.

18. The improved photoionization ion mobility spectrometer of claim 1 further comprising a means for introducing a dopant into said photoionization chamber, wherein said dopant comprises chemical species having an ionization potential less than the maximum photon energy corresponding to the shortest wavelength of the light emitted by said flashlamp means and wherein said flashlamp means comprises a flashlamp filled with krypton and sealed with a magnesium fluoride window, and said photon energy is about 10.0 to 10.2 eV.

19. The improved photoionization ion mobility spectrometer of claim 18 wherein said dopant is acetone.

20. The improved photoionization ion mobility spectrometer of claim 1 wherein said ionized gas sample is either positively charged or negatively charged.

21. The improved photoionization ion mobility spectrometer of claim 1 further comprising a means for introducing a dopant into said photoionization chamber and wherein said dopant comprises chemical species which has an ionization potential greater than the maximum photon energy corresponding to the shortest emitted by said flashlamp means but can be photoionized through indirect means.

22. A method for improving the sensitivity of photoionization ion mobility spectrometer, said photoionization ion mobility spectrometer having photoionization means, a photoionization chamber, a drift chamber, drift gas inlet passage for introducing a drift gas into the drift chamber, carrier gas inlet passage for introducing a carrier gas containing gas sample to be analyzed into the photoionization chamber, wherein said improvement comprises:
(a) using a flashlamp means as the photoionization mean;
(b) said flashlamp comprising a pulse transformer and a flashlamp; and
(c) said flashlamp having a pulse duration in the microsecond range.

23. The method for improving the sensitivity of photoionization ion mobility spectrometer of claim 22 further comprises the step of introducing a dopant into the carrier gas, said dopant comprising chemical species having an ionization potential less than the photon energy corresponding to the wavelength of the light of maximum intensity emitted by said flashlamp means.

24. The method of claim 23 wherein said dopant comprises chemical species which has an ionization potential greater than the photon energy corresponding to the wavelength of the light of maximum intensity emitted by said flashlamp means but can be photoionized through indirect means.

* * * * *